(12) United States Patent
Trink et al.

(10) Patent No.: US 10,329,535 B2
(45) Date of Patent: Jun. 25, 2019

(54) SYSTEM AND METHOD FOR COLD ATMOSPHERIC PLASMA TREATMENT ON CANCER STEM CELLS

(71) Applicant: U.S. Patent Innovations, LLC, Takoma Park, MD (US)

(72) Inventors: Barry Trink, Baltimore, MD (US); Michael Keidar, Baltimore, MD (US); Jerome Canady, Lakeland, FL (US)

(73) Assignee: US Patent Innovations, LLC, Takoma Park, MD (US)

( * ) Notice: Subject to any disclaimer, the term of this patent is extended or adjusted under 35 U.S.C. 154(b) by 356 days.

(21) Appl. No.: 15/392,596

(22) Filed: Dec. 28, 2016

(65) Prior Publication Data

US 2017/0183632 A1 Jun. 29, 2017

Related U.S. Application Data

(60) Provisional application No. 62/271,378, filed on Dec. 28, 2015.

(51) Int. Cl.
*A61B 18/00* (2006.01)
*C12N 5/095* (2010.01)
(Continued)

(52) U.S. Cl.
CPC .......... *C12N 5/0695* (2013.01); *A61B 18/042* (2013.01); *C12N 5/0682* (2013.01);
(Continued)

(58) Field of Classification Search
CPC ........ A61B 18/042; A61B 2018/00583; C12N 2500/02; C12N 5/0682; C12N 5/0693; C12N 5/0695; H05H 1/46
See application file for complete search history.

(56) References Cited

U.S. PATENT DOCUMENTS 6,099,523 A * 8/2000 Kim .................... A61B 18/042
 606/40
8,471,171 B2 * 6/2013 Price ........................ H05H 1/46
 219/121.48

(Continued)

OTHER PUBLICATIONS

Keidar M., Walk R., Shashurin A., Srinivasan P., Sandler A., Dasgupta S., Ravi R., Guerrero-Preston R. and Trink B., "Cold plasma selectivity and the possibility of a paradigm shift in cancer therapy," Br. J. Cancer 2011;105:1295-301.

(Continued)

*Primary Examiner* — Michael F Peffley
(74) *Attorney, Agent, or Firm* — 24IP Law Group USA, PLLC; Timothy Dewitt

(57) ABSTRACT

A method for treating cancer stem cells with cold atmospheric plasma using a cold atmospheric plasma system The method comprises the steps of placing an exit port of a cold plasma delivery device 5 cm or less from target cancer stem cells, flowing the inert gas from the source through the housing at a flow rate of 5-10 ml/minute, applying electrosurgical energy of 2-5 kV at a frequency of 20-35 kHz to at least one of the central electrode and the ring electrode to produce a cold plasma jet from the exit port, directing the cold plasma jet onto the target cancer stem cells, and applying the cold plasma jet onto the target cancer stem cells for at least 2 minutes. In a preferred embodiment the inert gas is helium.

6 Claims, 3 Drawing Sheets

(51) Int. Cl.
  *C12N 5/071* (2010.01)
  *C12N 5/09* (2010.01)
  *A61B 18/04* (2006.01)
  *H05H 1/46* (2006.01)

(52) U.S. Cl.
  CPC ............ *C12N 5/0693* (2013.01); *H05H 1/46* (2013.01); *A61B 2018/00583* (2013.01); *C12N 2500/02* (2013.01)

(56) References Cited

U.S. PATENT DOCUMENTS

| | | | | |
|---|---|---|---|---|
| 9,656,095 | B2* | 5/2017 | Watson | H01J 37/32825 |
| 9,744,372 | B2* | 8/2017 | Jacofsky | A61M 37/00 |
| 9,999,462 | B2* | 6/2018 | Canady | A61B 18/042 |
| 2014/0378892 | A1* | 12/2014 | Keidar | A61N 1/44 604/23 |

OTHER PUBLICATIONS

Abelson S., Shamai Y., Berger L., Shouval R., Skorecki K., Tzukerman M., "Intratumoral heterogeneity in the selfrenewal and tumorigenic differentiation of ovarian cancer," Stem cells 2012;30:415-24.

Abelson S., Shamai Y., Berger L., Skorecki K., Tzukerman M., "Niche-dependent gene expression profile of intratumoral heterogeneous ovarian cancer stem cell populations," PloS one 2013;8:e83651.

Marusyk A., Polyak K., "Tumor heterogeneity: causes and consequences," Biochim Biophys Acta 2010;1805:105-117.

Shackleton M., Quintana E., Fearon E.R., Morrison S.J, "Heterogeneity in cancer: cancer stem cells versus clonal evolution," Cell 2009;138: 822-829.

Yap T.A., Gerlinger M., Futreal P.A., Pusztai L., Swanton C., "Intratumor heterogeneity: seeing the wood for the trees," Sci Transl Med 2012;4:127ps110.

* cited by examiner

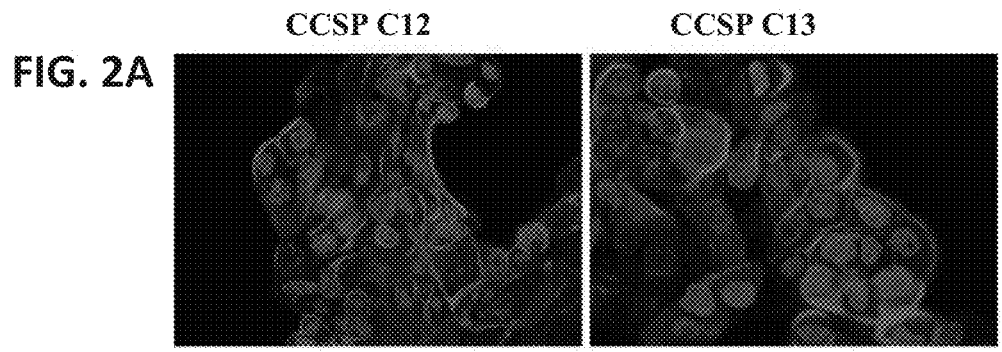
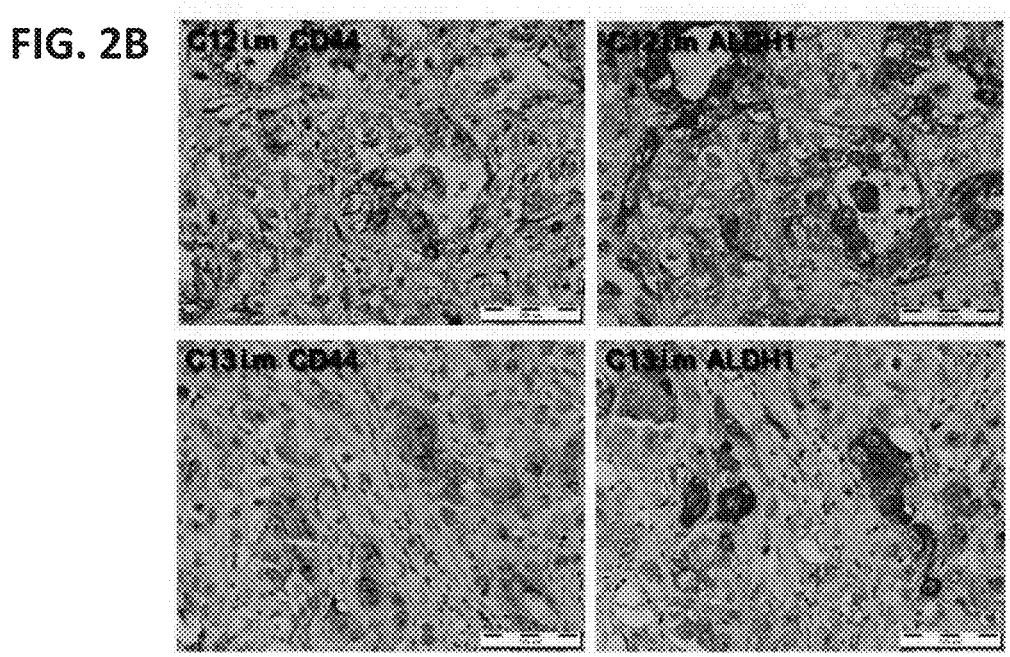
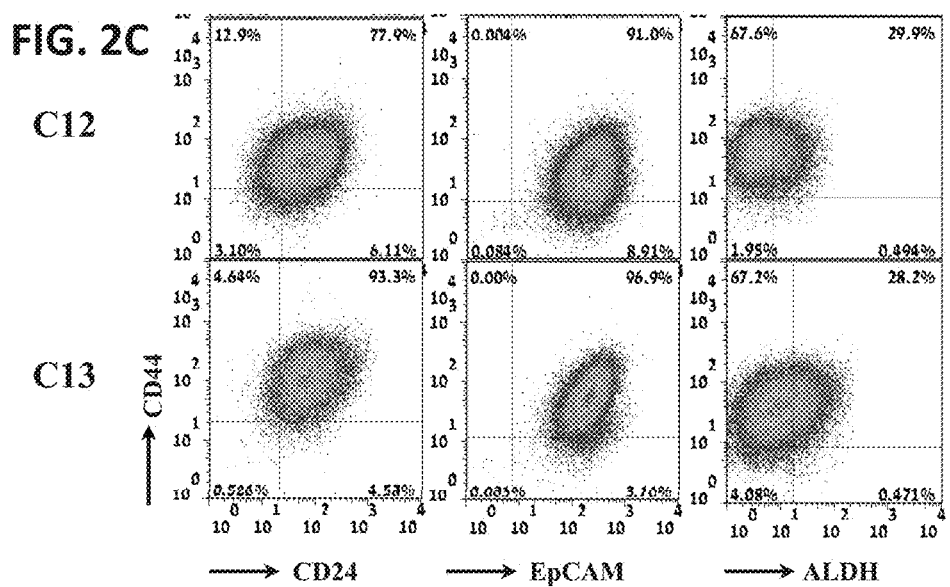
FIG. 2A
FIG. 2B
FIG. 2C

SYSTEM AND METHOD FOR COLD ATMOSPHERIC PLASMA TREATMENT ON CANCER STEM CELLS

CROSS-REFERENCE TO RELATED APPLICATIONS

The present application claims the benefit of the filing date of U.S. Provisional Patent Application Ser. No. 62/271,378 filed by the present inventors on Dec. 28, 2015. The present application also is related to U.S. patent application Ser. No. 14/934,129, filed on Nov. 5, 2015, and entitled "System And Method For Selective Ablation Of Cancer Cells With Cold Atmospheric Plasma." The aforementioned patent application is hereby incorporated by referenced in its entirety.

STATEMENT REGARDING FEDERALLY SPONSORED RESEARCH OR DEVELOPMENT

None.

BACKGROUND OF THE INVENTION

Field of the Invention

The present invention relates to plasma treatment of cancer stem cells.

Brief Description of the Related Art

Plasma is an ionized gas that is generated in high-temperature laboratory conditions. Recent developments in plasma physics research has led to the production of cold plasmas with ion temperature close to room temperature. See, Laroussi M., Kong M., Morfill G. and Stolz W., 2012 Plasma Medicine (Cambridge: Cambridge University Press); Fridman A. and Friedman G., 2013 Plasma Medicine (New York: Wiley); and Keidar, M, and Beilis, I., 2013 Plasma Engineering: Application in Aerospace, Nanotechnology and Bionanotechnology (Oxford: Elsevier). Initial studies demonstrated the non-aggressive nature of the cold plasma whereby plasma can interact with organic materials without causing thermal/electric damage to the cell surface. These developments opened up new avenues for plasma applications in biological settings including wound healing, disinfection and more recently in cancer research. This has led to the development of a new field in biological research known as plasma medicine.

Plasma medicine is a relatively new scientific field emerged from research in application of a low-temperature (or cold) atmospheric plasmas in bioengineering. It became apparent that cold atmospheric plasma (CAP) interaction with tissue allows targeted cell removal without necrosis, i.e. cell disruption. In fact, it was demonstrated that CAP affects cells via a programmable process called apoptosis, a multi-step process leading to cell death. Recent cold plasma therapy studies both in vivo and in vitro exhibited apoptosis in bacterial and mammalian cells including various types of cancer cells. The first in vivo demonstration of CAP anti-cancer potential was performed by Vandamme et al on human U87 glioblastoma xenotransplants. See, Vandamme M., Robert E., Pesnel S., Barbosa E., Dozias S., Sobilo J., Lerondel S., Le Pape A. and Pouvesle J. M., "Antitumor effect of plasma treatment on U87 glioma xenografts: preliminary results," Plasma Process. Polym. 2010; 7:264. Vandamme M., Robert E., Lerondel S., Sarron V., Ries D., Dozias S., Sobilo J., Gosset D., Kieda C., Legrain B., Pouvesle J. M., Pape A. L., "ROS implication in a new antitumor strategy based on non-thermal plasma," Int. J. Cancer. 2012; 130:2185-94. This study indicated that treatment over multiple days has been effective in reducing tumor volume and increasing survival time through ROS-mediated apoptosis. In another study the anti-tumor action of CAP was demonstrated on a syngenic mouse melanoma and heterotopic human bladder cancer xenograft models. Keidar M., Walk R., Shashurin A., Srinivasan P., Sandler A., Dasgupta S., Ravi R., Guerrero-Preston R. and Trink B., "Cold plasma selectivity and the possibility of a paradigm shift in cancer therapy," Br. J. Cancer 2011; 105:1295-301. The ability of CAP to ablate the tumor in a single treatment was one of the most interesting results demonstrated. In particular, tumors of about 5 mm in diameter were ablated after about 2 min of a single treatment.

Nevertheless, it is now widely appreciated that a single tumor is basically comprised of heterogeneous cell populations, each of which displays a diverse cellular morphology, phenotypic expression, tumor initiation capacities and inherent or acquired resistance to anti-cancer drugs. See, Abelson S., Shamai Y., Berger L., Shouval R., Skorecki K., Tzukerman M., "Intratumoral heterogeneity in the self-renewal and tumorigenic differentiation of ovarian cancer," Stem cells 2012; 30:415-24 Abelson S., Shamai Y., Berger L., Skorecki K., Tzukerman M., "Niche-dependent gene expression profile of intratumoral heterogeneous ovarian cancer stem cell populations," PloS one 2013; 8:e83651; Kreso A., O'Brien C. A., van Galen P., Gan O. I., Notta F., Brown A. M., Ng K., Ma J., Wienholds E., Dunant C., Pollen A., Gallinger S., McPherson J., Mullighan C. G., Shibata D., Dick J. E., "Variable clonal repopulation dynamics influence chemotherapy response in colorectal cancer," Science 2013; 339: 543-548; and O'Connor J. P., Rose C. J., Waterton J. C., Carano R. A., Parker G. J., Jackson A., "Imaging intratumor heterogeneity: role in therapy response, resistance, and clinical outcome," 2015; 21:249-57. The aggressiveness and ingenuity of human cancers emanate mainly from such complex intratumoral heterogeneity, which in turn has been attributed to genetic and epigenetic changes coupled with adaptive responses to the tumor microenvironment. Accumulating evidence demonstrates that the model of 'cancer stem cells' (CSC) and the clonal evolution model, mutually contribute to intratumoral heterogeneity, as CSC themselves undergo clonal evolution. See, Marusyk A., Polyak K., "Tumor heterogeneity: causes and consequences," Biochim Biophys Acta 2010; 1805:105-117; Polyak K., Haviv I., Campbell I. G., "Co-evolution of tumor cells and their microenvironment," Trends Genet 2009; 25:30-38; Shackleton M., Quintana E., Fearon E. R., Morrison S. J, "Heterogeneity in cancer: cancer stem cells versus clonal evolution," Cell 2009; 138: 822-829; and Yap T. A., Gerlinger M., Futreal P. A., Pusztai L., Swanton C., "Intratumor heterogeneity: seeing the wood for the trees," Sci Transl Med 2012; 4:127ps110. The continuous accumulation of mutations generates heterogeneity of cells within a solid tumor and its metastases, and may reflect the process whereby certain subsets of tumor cells become more aggressive in the process of tumor progression.

The limitation of conventional anti-cancer therapies may lead to treatment failure and cancer recurrence mainly due to drug resistance and self-renewal capacities of CSC which are responsible for resistance to standard oncology treatments. Reya T., Morrison S. J., Clarke M. F., Weissman I. L., "Stem cells, cancer, and cancer stem cells," Nature. 2001; 414:105-111.

SUMMARY OF THE INVENTION

In a preferred embodiment, the present invention is a method for treating cancer stem cells with cold atmospheric plasma using a cold atmospheric plasma system having a source of high voltage power, a source of an inert gas, and a cold plasma delivery apparatus having a housing, a channel within the housing connected to the source of insert gas and having an exit port through which the inert gas exits the housing, a central electrode within the housing, and an outer ring electrode outside the housing. The method comprises the steps of placing the exit port 5 cm or less from target cancer stem cells, flowing the inert gas from the source through the housing at a flow rate of 5-10 ml/minute, applying electrosurgical energy of 2-5 kV at a frequency of 20-35 kHz to at least one of the central electrode and the ring electrode to produce a cold plasma jet from the exit port, directing the cold plasma jet onto the target cancer stem cells, and applying the cold plasma jet onto the target cancer stem cells for at least 2 minutes. In a preferred embodiment the inert gas is helium.

In another preferred embodiment, the present invention is a method for treating cancer stem cells with cold atmospheric plasma using a cold atmospheric plasma system for producing a cold atmospheric plasma jet, the cold atmospheric plasma system having a source of high voltage power, a source of an inert gas, and a cold plasma delivery apparatus having a housing, a channel within the housing connected to the source of insert gas and having an exit port through which the inert gas exits the housing, a central electrode within the housing, and an outer ring electrode outside the housing. The method comprises the steps of applying a cold plasma jet from the cold atmospheric plasma onto target cancer stem cells on at least two different days in a period of four consecutive days for at least 2 minutes each time. Each application of cold atmospheric plasma to the target cancer stem cells comprises the steps of placing the exit port 5 cm or less from target cancer stem cells, flowing the inert gas from the source through the housing at a flow rate of 5-10 ml/minute, applying electrosurgical energy of 2-5 kV at a frequency of 20-35 kHz to at least one of the central electrode and the ring electrode to produce a cold plasma jet from the exit port, directing the cold plasma jet onto the target cancer stem cells, applying the cold plasma jet onto the target cancer stem cells for at least 2 minutes. The inert gas may be helium. In a further embodiment, the step of applying a cold plasma jet over at least two days in a period of four consecutive days comprises applying the cold plasma jet to the target cancer cells on each of the first day of the four consecutive days, the second day of the four consecutive days, and the fourth day of the four consecutive days.

It was recently demonstrated that cancer initiating cells (CICs) underwent apoptosis at a comparable level to non-CIC (21). For this reason, we sought to examine the effect of CAP on two different ovarian cancer stem cells derived from a single tumor to determine its feasibility in eradication of CSC in vitro.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 2A-C are images of six different cancer cell subpopulations (CCSPs) from a tumor of a single patient.

DETAILED DESCRIPTION OF THE PREFERRED EMBODIMENTS

To overcome the ineffectiveness of traditional cancer therapies that lead to tumor recurrence and metastasis, it is important to develop efficient anti-cancer treatments. The combination of conventional anticancer drugs with CSC targeting treatment, may offer a promising strategy for management and eradication of different types of cancers.

Cold plasma is an ionized gas with ion temperature close to room temperature and can be used to selectively attack cancerous tissue without damaging normal cells and reduce tumor size in-vivo. The paper entitled "Cold Plasma Selectivity and the Possibility of a Paradigm Shift in Cancer Therapy," to M. Keidar, et al., British Journal of Cancer (2011) 105, pp. 1295-1301 which is part of the specification, discloses the use of cold plasma generally for cancer treatment.

Figure 1:
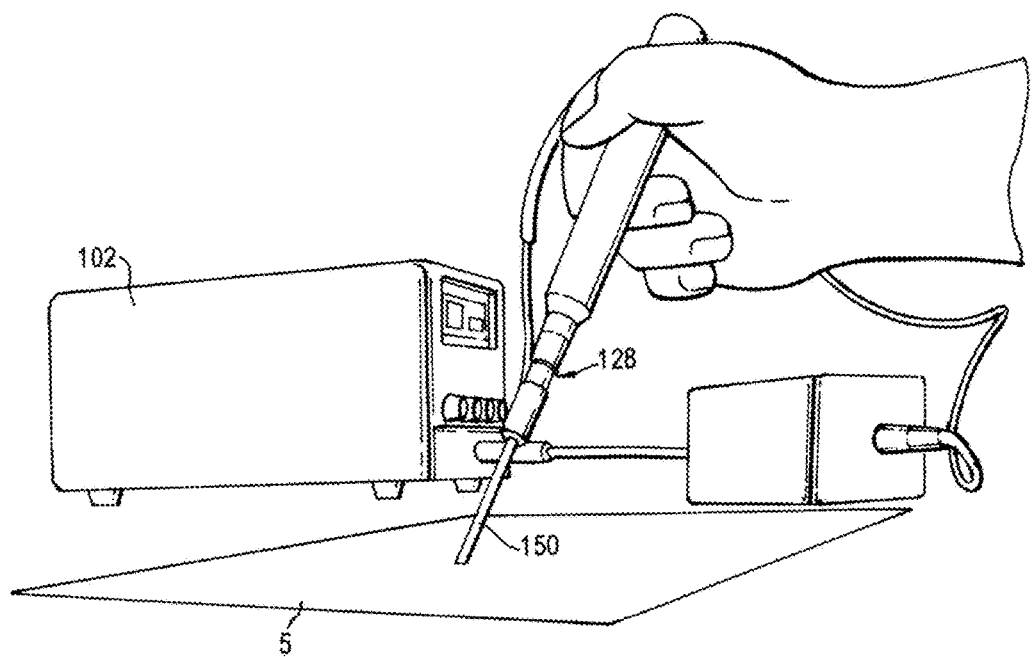
FIG. 1 is a perspective view of a setup of a cold plasma system in accordance with a preferred embodiment of the present invention.

FIG. 1 shows an exemplary cold plasma therapy system. The system includes a power supply 102, controller, gas source, and a delivery mechanism. The delivery mechanism has a body and a central electrode located at the center of the body 121 at the interior of the body at the central longitudinal axis body. The central electrode enters the body at a sealed proximal end of the body and extends the length of the body to approximately the discharge end. A sealing plug (such as rubber) is located over the open end of the syringe to prevent the gas from escaping from the inside of the syringe.

The electrode is entirely surrounded by insulation except at its distal end which is exposed and in contact with gas and plasma. The insulation allows the power to be focused at the exposed distal end to lead to the discharge at the end. The central electrode and surrounding insulation, has a proximal end that extends to the outside of the body through an opening in the plug. The plug opening forms a friction fit with the insulation, so that gas does not escape from the body. Thus, the central electrode is positioned inside the body, except for the portion of the proximal end of the electrode that extends into and through the plug. In this manner, the plug opening holds the electrode and insulation in position within the body, with the distal end of the electrode facing a distal nozzle of the body.

In addition, an annular outer ring electrode 128 is located about a portion of the narrow neck at the outside of the body. The electrodes are high voltage electrodes. The central electrode can be, for instance, a wire, and the insulation 127 can be a ceramic insulation. The power supply 102 is electrically connected to the electrodes and provides a high voltage supply to the electrodes through the cables. The controller regulates the voltage and frequency that is applied to the central electrode and the ring electrode. An optional adapter may interface the delivery device with high voltage transformer 102.

The gas source is in gas communication with the delivery device through a supply tube. The supply tube is connected to a port located in a side of the body. The supply tube can also be connected to the body through the adapter. The gas source can be pressurized, so that gas travels through the supply tube into the inside space of the body. A separate gas controller (not shown) can be provided to control the flow rate of the gas in the supply tube, or the gas controller can be integrated with the controller. The gas then continues through the body and exits the body through the neck and nozzle (an exit port) at the discharge end as a jet or stream flow 150.

As the gas enters the discharge area and the neck of the body, the electrodes excite the gas, thereby ionizing the gas to form a cold plasma. In the embodiment shown, the gas is Helium, though other gases such as Nitrogen may be used. Thus, as the gas is discharged out of the distal nozzle, it is a cold plasma. The cold plasma jet or stream flow 150 diffuses over time. In accordance with a preferred embodiment of the invention, the plasma is provided at a flow rate of 17 liters per minute, with the voltage supply being 5 kV and 30 kHz. At that configuration, the plasma will have a high ionization as it exits the body. Accordingly, the body is preferably placed at a predetermined distance, which can be about 2 cm away from the target cells 5 being treated. The body allows the plasma to be targeted at desired cancer cells in the skin to selectively eradicate the cancerous cells and reduce tumor size. The body can be utilized, for instance, to treat any cancer type which is close to the skin and can be applied without surgery, such as breast, colon, lung, bladder, or oral. With surgery, the invention can be applied to any tumor. In accordance with an illustrative embodiment, the flow rate can be 10-17 liters/min., with a voltage of 2-5 kV and frequency of 30-35 KHz, and a nozzle of 3-5 mm diameter and a distance between the central electrode 126 and the ring electrode 128 of 5-10 mm. The plasma preferably has a density of about $3 \times 10^{13}$ to $9 \times 10^{13}$ $cm^{-3}$, such as discussed in "Temporary-resolved measurement of electron density in small atmospheric plasmas," to Shashurin et al., Applied Physics Letters 96, 171502 (2010), which is hereby incorporated by reference.

At the predetermined distance, the plasma will have diffused to a desirable level. However, the intensity of the plasma will continue to decrease as the target area is moved further from the body, and the plasma will be essentially entirely dissipated at a distance of 5 cm from the body. The plasma is well collimated the entire length up to about 5 cm from the body. The plasma jet stream is discontinuous and represents a series of propagating plasma bundles.

It should be apparent, however, that other suitable settings can be utilized. Preferably, however, the power supply 102 has a voltage from about 2-5 kV with a frequency of about 30 kHz, and the gas has a flow rate of about 2-17 l/min.

EXAMPLES

Cold Plasma Treatments

Cold plasma treatments were carried out at HV in the range of 3-5 kV, 20 kHz frequency, helium flow in the range 10-20 lmin$^{-1}$, distance from plasma source to cells of about 1 cm and treatment durations of about 30 s.

Electrical measurements were performed with a Tektronix TDS3014C Digital Phosphor Oscilloscope. Emission spectra were recorded with an optical fiber which was connected to a fiber optic spectrometer (EPP2000-HR, Stella Net, measurements can be made in UV-VIS-NIR ranges from 190-2200 nm). The feeding gas was helium.

Derivation of Ovarian Cancer Cell Subpopulations

Collection of ascites fluid was performed with a written informed consent of a 64 year old patient diagnosed with stage IV Ovarian Clear Cell Carcinoma and the protocol was approved by the institutional Ethics Review Committee of the Rambam Medical Center. Six different cancer cell subpopulations, clonally expanded from a single cell, including CCSP C12 and C13, were derived from the malignant ovarian ascites and propagated in culture as previously described. Although maintained in culture for more than 6 years, cell cultures are repeatedly initiated from frozen stocks every 3-4 months, and the CCSPs durably and consistently maintain the "bona fide" ovarian cancer characteristics, CSC characteristics and xenografted tumor histological phenotype. See, Katz E., Skorecki K., Tzukerman M., "Niche-dependent tumorigenic capacity of malignant ovarian ascites-derived cancer cell subpopulations," Clin. Cancer Res. 2009; 15: 70-80.

CAP Sensitivity Assay

CCSP C12 and C13 cancer stem cells were plated in triplicates on fibronectin-coated 12-well plates ($5 \times 10^3$ cells per well) in RPMI-1640 supplemented with 20% FBS, 1% penicillin/streptomycin and 1%-glutamine. Medium was replaced every other day. Cells were treated with CAP for 1, 2, and 3 minutes at days 5, 6 and 8 following seeding. For control, non-treated cells and cells treated with Helium were used. All cells were harvested on day 11 (from seeding) and counted.

RESULTS

Cold Plasma Source

The cold plasma source is equipped with a pair of high-voltage (HV) electrodes, a central electrode and an outer ring electrode as shown in FIG. 1. Electrodes are connected to a secondary coil of HV resonant transformer operating at a voltage of about 2-5 kV and a frequency of about 30 kHz, with a helium flow rate of about 5-10 lmin$^{-1}$. The visible plasma jet had a length of approximately 5 cm and was well collimated along the entire length. According to previous studies (23) the plasma jet is discontinuous and represents a series of propagating plasma bullets. See, Shashurin A., Keidar M., Bronnikov S., Jurjus R. A. and Stepp M. A., 2008 Appl. Phys. Lett. 92 181501

Ovarian Cancer-Derived Heterogeneous CSC.

Ovarian clear cell carcinoma (OCCC), is characterized by striking intratumoral morphologic heterogeneity, including cells with features of advanced ovarian structural variation on the one hand, and cells with features of tumorigenic differentiation (e.g. invasion, proliferation) and corresponding cell surface and intracellular marker heterogeneity. See, Czernobilsky B., Silverman B. B., Enterline H. T., "Clear-cell carcinoma of the ovary: A clinicopathologic analysis of pure and mixed forms and comparison with endometrioid carcinoma," Cancer 1970; 25: 762-772; Montag A. G., Jenison E. L., Griffiths C. T., Welch W. R., Lavin P. T., Knapp R. C., "Ovarian clear cell carcinoma: A clinicopathologic analysis of 44 cases," Int J Gynecol Pathol 1989; 8: 85-96; Tan D. S., Kaye S., "Ovarian clear cell adenocarcinoma: a continuing enigma," J. Clin. Pathol 2007; 60: 355-360; Kobel M., Kalloger S. E., Carrick J., Huntsman D., Asad H., Oliva E., Ewanowich C. A., Soslow R. A., Gilks C. B., "A limited panel of immunomarkers can reliably distinguish between clear cell and high-grade serous carcinoma of the ovary," Am J Surg Pathol 2009; 33: 14-21; and DeLair D., Oliva E., Kobel M., Macias A., Gilks C. B., Soslow R. A., "Morphologic spectrum of immunohistochemically characterized clear cell carcinoma of the ovary: a study of 155 cases," Am J Surg Pathol 2011; 35: 36-44. We have isolated and characterized six different cancer cell subpopulations (CCSPs) from a tumor of a single patient, and demonstrated niche dependent tumorigenic capacities and histological phenotypes which cumulatively recapitulate the full spectrum of tumor heterogeneity.

The six CCSPs, each clonally expanded from a single cell, demonstrate striking intratumoral phenotypic heterogeneity that is dynamically dependent on the tumor growth microenvironment. The six CCSPs, were characterized as ovarian CSC by virtue of functional and phenotypic expression of CD44+CD24+EpCAM+ and ALDH1 activity (FIG. 2).

To examine the effect of CAP on CSC we focused on two distinct cancer cell subpopulations, CCSP C12 and C13 which exhibit the extremes of tumorigenic phenotypic attributes and niche-dependent self-renewal capacity. C12-derived tumors are characterized by an abundance of highly differentiated ovarian structures while C13-derived tumors exhibit poor ovarian structural differentiation. In addition, C13 preserves its capacity for self-renewal as demonstrated by in vivo perpetuation of tumorigenic cancer cells both in the murine and the in the hESC-based in vivo model while C12 fails to perpetuate tumorigenic cells in the murine tissue but generates highly aggressive and invasive tumors within the hESC-based in vivo model. In the light of this striking effect, we aim to examine the effect of CAP in eradication of these two populations of patient-derived ovarian tumor CSC.

In-Vitro Cold Plasma Treatment of Cancer Stem Cells

Figure 3A:
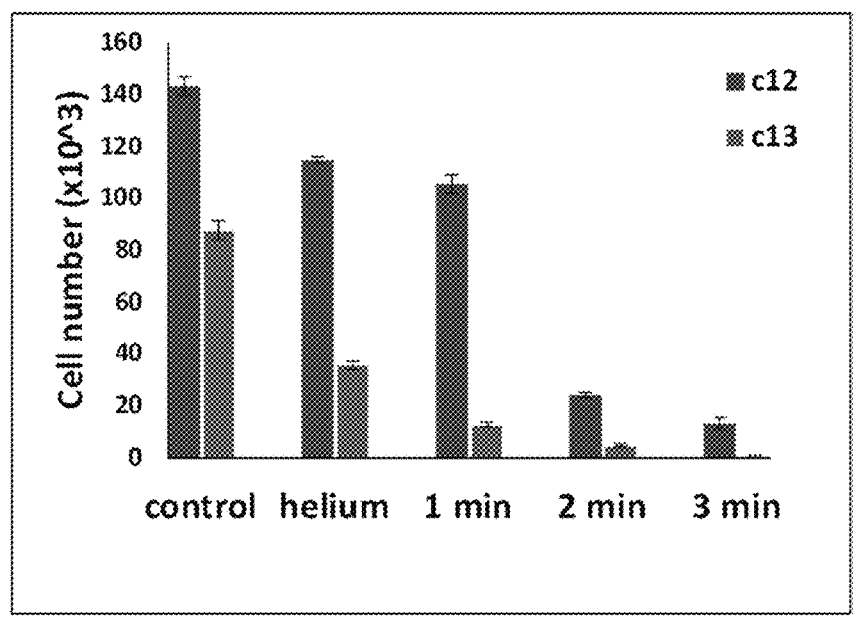
FIGS. 3A-B are graphs illustrating the results obtained in the examples described herein.
Figure 3B:
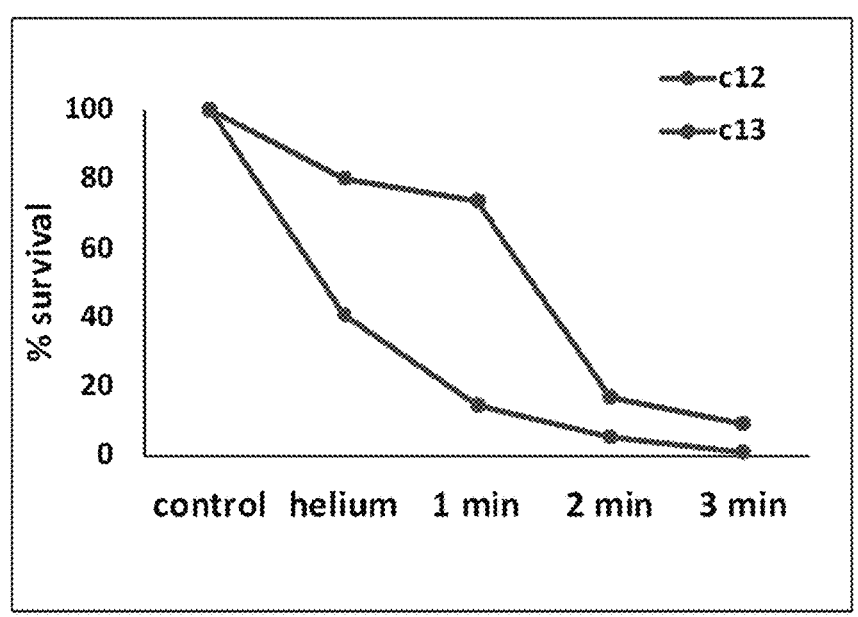

To examine the effect of plasma treatment on CCSPs C12 and C13 in vitro, cells were seeded on day 1 as described in Table 1. The cells were treated with plasma on days 5, 6 and 8 for 1, 2 or 3 minutes and counted on day 11 after seeding. Controls were either untreated cells or cells treated with helium for 3 minutes. As seen in Table 1 the results obtained demonstrate that both CCSPs C12 and C13 were sensitive to plasma to varying degrees. The C13 cells were very sensitive to the plasma treatment whereas the C12 to a lesser degree (FIG. 3). Taken together, these results might suggest the effectiveness of CAP treatment in eradication of CSC in ovarian patient tumors.

Discussion and Concluding Remarks

Over the last several years a convincing evidence of CAP efficacy in cancer application has been demonstrated. Various aspects of CAP-based cancer therapy were studied worldwide including the role of reactive species (reactive oxygen and nitrogen), cell cycle modification, in vivo application for solid tumors, CAP interaction with cancer cells in conjunction with nanoparticles and most recently first clinical application. To this end, two best known effects of plasma such as plasma-induced apoptosis and the decrease of cell migration velocity, have important implications in cancer. These two most known effects of plasma can lead to localizing the cancer-affected area of the tissue and to decreasing the metastatic development. In this study, we explored the role of CAP in treating CSC which is another exciting application of this new therapy.

Intratumoral heterogeneity challenges existing paradigms for anti-cancer therapy. If such heterogeneity also includes self-renewing cells which sustain the tumor mass, feed into progressive tumorigenic differentiation and account for tumor recurrence—then attempts to eradicate a single stable self-renewing subpopulation within any given tumor will prove futile. Therefore any novel method which leads to the destruction of these CSC will enhance our ability to treat cancer.

The molecular mechanism and cancer cell response to the CAP jet is not well understood. It is known that normal cells often produce substantially less reactive oxygen and nitrogen species (RONS) than tumor cells. Thus one can suggest that additional amounts of RONS from the CAP jet would make a dramatic difference to the response of normal and cancer cells to CAP, thereby crossing this survival threshold for tumor cells and leading to cell death through DNA damage, apoptosis or cell cycle arrest. It is plausible to hypothesize that effect of CAP and CSC described in this paper is associated with RONS generation leading to oxidative stress. Thus future studies should involve intracellular RONS measurements.

The results obtained in this study demonstrate that both type of heterogeneous CSC populations derived from a single tumor are sensitive to the effects of plasma treatment albeit to varying degrees. It is interesting to note that the more aggressive CSC population C13, was more sensitive to CAP treatment than C12. We postulate that C13 sensitivity might result from the fact that these are smaller cells with a higher proliferation capacity as compare to C12 CSC populations. Taken together our results indicate the sensitivity of heterogeneous populations of CSC derived from a single ovarian patient tumor and suggest the efficiency of CAP as an effective anti-cancer treatment. Further development of CAP technology for CSC treatment should be associated with in vivo studies.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for treating cancer stem cells with cold atmospheric plasma using a cold atmospheric plasma system having a source of high voltage power, a source of an inert gas, and a cold plasma delivery apparatus having a housing, a channel within said housing connected to said source of insert gas and having an exit port through which said inert gas exits said housing, a central electrode within said housing, and an outer ring electrode outside said housing, the method comprising the steps of:
   placing said exit port 5 cm or less from target cancer stem cells;
   flowing said inert gas from said source through said housing at a flow rate of 5-10 ml/minute;
   applying a voltage of 2-5 kV at a frequency of 20-35 kHz to at least one of said central electrode and said ring electrode to produce a cold plasma jet from said exit port;
   directing said cold plasma jet onto the target cancer stem cells; and
   applying said cold plasma jet onto said target cancer stem cells for at least 2 minutes.

2. The method according to claim 1 wherein said inert gas comprises helium.

3. A method for treating cancer stem cells with cold atmospheric plasma using a cold atmospheric plasma system for producing a cold atmospheric plasma jet, said cold atmospheric plasma system having a source of high voltage power, a source of an inert gas, and a cold plasma delivery apparatus having a housing, a channel within said housing connected to said source of insert gas and having an exit port through which said inert gas exits said housing, and a central electrode within said housing, the method comprising the steps of:
- applying a cold plasma jet from said cold atmospheric plasma system onto target cancer stem cells on at least two different days in a period of four consecutive days, wherein each application of cold atmospheric plasma to said target cancer stem cells comprises the steps of:
- placing said exit port 5 cm or less from target cancer stem cells;
- flowing said inert gas from said source through said housing at a flow rate of 5-10 ml/minute;
- applying a voltage of 2-5 kV at a frequency of 20-35 kHz to said central electrode to produce a cold plasma jet from said exit port;
- directing said cold plasma jet onto the target cancer stem cells;
- applying said cold plasma jet onto said target cancer stem cells for at least 2 minutes.

4. The method according to claim 3 wherein said inert gas comprises helium.

5. The method according to claim 3 wherein said step of applying a cold plasma jet over at least two days in a period of four consecutive days comprises applying said cold plasma jet to said target cancer cells on each of the first day of said four consecutive days, the second day of said four consecutive days, and the fourth day of said four consecutive days.

6. A method for treating cancer stem cells with cold atmospheric plasma using a cold atmospheric plasma system having a source of high voltage power, a source of an inert gas, and a cold plasma delivery apparatus having a housing, a channel within said housing connected to said source of insert gas and having an exit port through which said inert gas exits said housing, and a central electrode within said housing, the method comprising the steps of:
- placing said exit port 5 cm or less from target cancer stem cells;
- flowing said inert gas from said source through said housing at a flow rate of 5-10 ml/minute;
- applying a voltage of 2-5 kV at a frequency of 20-35 kHz to said central electrode to produce a cold plasma jet from said exit port;
- directing said cold plasma jet onto the target cancer stem cells; and
- applying said cold plasma jet onto said target cancer stem cells for at least 2 minutes.

* * * * *